United States Patent
Fowler et al.

(10) Patent No.: US 9,456,604 B2
(45) Date of Patent: Oct. 4, 2016

(54) HERBICIDE COMPOSITION

(75) Inventors: Jeffrey David Fowler, Greensboro, NC (US); Gavin John Hall, Bracknell (GB); Carl Andrew Formstone, Bracknell (GB); Stefan Michael Haas, Bracknell (GB)

(73) Assignee: Syngenta Crop Protection, LLC, Greensboro, NC (US)

( * ) Notice: Subject to any disclaimer, the term of this patent is extended or adjusted under 35 U.S.C. 154(b) by 247 days.

(21) Appl. No.: 12/997,217

(22) PCT Filed: Jun. 8, 2009

(86) PCT No.: PCT/GB2009/001426
§ 371 (c)(1),
(2), (4) Date: Mar. 4, 2011

(87) PCT Pub. No.: WO2010/001084
PCT Pub. Date: Jan. 7, 2010

(65) Prior Publication Data
US 2011/0143938 A1 Jun. 16, 2011

(30) Foreign Application Priority Data
Jun. 9, 2008 (GB) .................................. 0810554.6

(51) Int. Cl.
| A01N 43/40 | (2006.01) |
| A01N 25/02 | (2006.01) |
| A01N 37/22 | (2006.01) |
| A01N 37/26 | (2006.01) |
| A01N 37/40 | (2006.01) |
| A01N 41/06 | (2006.01) |
| A01N 41/10 | (2006.01) |
| A01N 43/10 | (2006.01) |
| A01N 43/64 | (2006.01) |
| A01N 43/70 | (2006.01) |
| A01N 47/36 | (2006.01) |
| A01N 57/20 | (2006.01) |

(52) U.S. Cl.
CPC .................................... *A01N 43/40* (2013.01)

(58) Field of Classification Search
CPC ....................................................... A01N 43/40
USPC .......................................................... 504/103
See application file for complete search history.

(56) References Cited

U.S. PATENT DOCUMENTS

2003/0104947 A1   6/2003   Woznica

FOREIGN PATENT DOCUMENTS

| EP | 1388285 | 2/2001 |
| WO | 0194339 | 12/2001 |
| WO | 2006003371 | 1/2006 |
| WO | WO 2006066871 A1 * | 6/2006 |

OTHER PUBLICATIONS

Ethanolamines Publication, Jan. 2003, The Dow Chemical Company, 20 pages.*
Green et al., "Increasing the biological activity of weak acid herbicides by increasing and decreasing the pH of the spray mixture", ASTM International Journal, ASTM International, US, vol. 2, No. 6, Jun. 1, 2005.

* cited by examiner

*Primary Examiner* — Sue Liu
*Assistant Examiner* — Andriae M Holt
(74) *Attorney, Agent, or Firm* — James Cueva

(57) ABSTRACT

The present invention relates to a method of selectively controlling weeds at a locus comprising crop plants and weeds, wherein the method comprises application to the locus of a weed controlling amount of an aqueous spray composition comprising a compound of formula (I) wherein $R^1$ is selected from the group consisting of $C_1$-$C_6$alkyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl, $C_1$-$C_6$haloalkyl, $C_1$-$C_4$alkoxy-$C_1$-$C_4$alkyl and $C_1$-$C_4$alkoxy- $C_1$-$C_4$alkoxy-$C_1$-$C_4$alkyl; and $R^2$ is $C_1$-$C_6$haloalkyl; or an agriculturally acceptable salt therefore; wherein in the pH of the spray composition is from about 5 to about 9. The invention further relates to a liquid substantially non-aqueous herbicide composition comprising a compound of formula (I) as defined above and a pH adjuster, and to the use of a pH adjuster to reduce the phytotoxicity of a compound of formula (I) in crop plants.

(I)

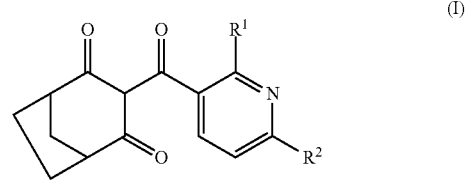

11 Claims, No Drawings

HERBICIDE COMPOSITION

This application is a 371 of International Application No. PCT/GB2009/001426 filed Jun. 8, 2009, which claims priority to GB 0810554.6 filed Jun. 9, 2008, the contents of which are incorporated herein by reference.

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Accordingly, chemical herbicides of many types have been disclosed in the literature. So-called "selective" herbicides are particularly desirable in that when they are applied to a locus comprising desirable vegetation (e.g. crop plants) and undesirable vegetation they selectively control the undesirable vegetation whilst leaving the crop plants substantially unharmed.

Compounds of formula (I) (see below) are selective herbicides which are known in the art (see WO01/94339 and EP-A-1388285). These compounds have been shown to provide good selective weed control in numerous crops—especially corn. It has now been surprisingly discovered that the selectivity of compounds of formula (I) can be further improved by applying them to the locus at a defined pH. In particular, the phytotoxicity observed in crops plants is substantially reduced.

Thus, according to the present invention there is provided a method of selectively controlling weeds at a locus comprising crop plants and weeds, wherein the method comprises application to the locus of a weed controlling amount of an aqueous spray composition comprising a compound of formula I

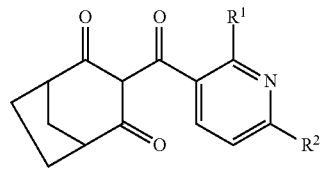

(I)

wherein $R^1$ is selected from the group consisting of $C_1$-$C_6$alkyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl, $C_1$-$C_6$-haloalkyl, $C_1$-$C_4$alkoxy-$C_1$-$C_4$alkyl and $C_1$-$C_4$alkoxy-$C_1$-$C_4$alkoxy-$C_1$-$C_4$alkyl; and $R^2$ is $C_1$-$C_6$haloalkyl;

or an agriculturally acceptable salt therefore;

wherein the pH of the aqueous spray composition is from about 5 to about 9.

In a preferred embodiment, component (a) is a compound of formula I wherein $R^1$=$C_1$-$C_4$alkoxy-$C_1$-$C_4$alkyl and $C_1$-$C_4$alkoxy-$C_1$-$C_4$alkoxy-$C_1$-$C_4$alkyl and $R^2$=$C_1$-$C_6$ fluoroalkyl. More preferred still is wherein component (a) is a compound of formula I wherein $R^1$=methoxy-ethyoxy-methyl and $R^2$=$CF_3$.

The rate of application of the compound of formula (I) to the locus can vary within a wide range and depends on the nature of the soil, the type of application (pre- or post-emergence; seed dressing; application to the seed furrow; no tillage application etc.), on the cultivated plant, the weed to be controlled, the prevailing climatic conditions and on other factors determined by the type of application, the time of application and the target crop. In general, the compound of formula (I) may be used at a rate of application of from 1 to 5000 g of active ingredient mixture/ha, more preferably 10 to 500 g of active ingredient mixture/ha, even more preferably 50 to 300 g of active ingredient mixture/ha.

In a preferred embodiment the pH of the spray composition is from about 6 to about 8, most preferably from about 7 to 8.

The aqueous spray composition may further comprise one or more additional pesticides, for example the compounds of formula I according to the invention can also be used in combination with other herbicides or plant growth regulators. Examples of such mixtures are (in which 'I' represents a compound of formula I). I+acetochlor, I+acifluorfen, I+acifluorfen-sodium, I+aclonifen, I+acrolein, I+alachlor, I+alloxydim, I+ametryn, I+amicarbazone, I+amidosulfuron, I+aminopyralid, I+amitrole, I+ammonium sulfamate, I+anilofos, I+asulam, I+atrazine, I+azafenidin, I+azimsulfuron, I+BCPC, I+beflubutamid, I+benazolin, I+bencarbazone, I+benfluralin, I+benfuresate, I+bensulfuron, I+bensulfuron-methyl, I+bensulide, I+bentazone, I+benzfendizone, I+benzobicyclon, I+benzofenap, I+bifenox, I+bilanafos, I+bispyribac, I+bispyribac-sodium, I+borax, I+bromacil, I+bromobutide, I+bromoxynil, I+butachlor, I+butamifos, I+butralin, I+butroxydim, I+butylate, I+cacodylic acid, I+calcium chlorate, I+cafenstrole, I+carbetamide, I+carfentrazone, I+carfentrazone-ethyl, I+CDEA, I+CEPC, I+chlorflurenol, I+chlorflurenol-methyl, I+chloridazon, I+chlorimuron, I+chlorimuron-ethyl, I+chloroacetic acid, I+chlorotoluron, I+chlorpropham, I+chlorsulfuron, I+chlorthal, I+chlorthal-dimethyl, I+cinidon-ethyl, I+cinmethylin, I+cinosulfuron, I+cisanilide, I+clethodim, I+clodinafop, I+clodinafop-propargyl, I+clomazone, I+clomeprop, I+clopyralid, I+cloransulam, I+cloransulam-methyl, I+CMA, I+4-CPB, I+CPMF, I+4-CPP, I+CPPC, I+cumyluron, I+cyanazine, I+cycloate, I+cyclosulfamuron, I+cycloxydim, I+cyhalofop, I+cyhalofop-butyl, I+2,4-D, I+daimuron, I+dalapon, I+dazomet, I+2,4-DB, I+I+desmedipham, I+dicamba, I+dichlobenil, I+dichlorprop, I+dichlorprop-P, I+diclofop, I+diclofop-methyl, I+diclosulam, I+difenzoquat, I+difenzoquat metilsulfate, I+diflufenican, I+diflufenzopyr, I+dimefuron, I+dimepiperate, I+dimethachlor, I+dimethametryn, I+dimethenamid, I+dimethenamid-P, I+dimethipin, I+dimethylarsinic acid, I+dinitramine, I+dinoterb, I+diphenamid, I+dipropetryn, I+diquat, I+diquat dibromide, I+dithiopyr, I+diuron, I+DNOC, I+2,4-DP, I+DPX-KJM-44 (development compound from DuPont), I+DSMA, I+endothal, I+EPTC, I+esprocarb, I+ethalfluralin, I+ethametsulfuron, I+ethametsulfuron-methyl, I+ethephon, I+ethofumesate, I+ethoxyfen, I+ethoxysulfuron, I+etobenzanid, I+fenoxaprop-P, I+fenoxaprop-P-ethyl, I+fentrazamide, I+ferrous sulfate, I+flamprop-M, I+flazasulfuron, I+florasulam, I+fluazifop, I+fluazifop-butyl, I+fluazifop-P, I+fluazifop-P-butyl, I+fluazolate, I+flucarbazone, I+flucarbazone-sodium, I+flucetosulfuron, I+fluchloralin, I+flufenacet, I+flufenpyr, I+flufenpyr-ethyl, I+flumetralin, I+flumetsulam, I+flumiclorac, I+flumiclorac-pentyl, I+flumioxazin, I+flumipropin, I+fluometuron, I+fluoroglycofen, I+fluoroglycofen-ethyl, I+fluoxaprop, I+flupoxam, I+flupropacil, I+flupropanate, I+flupyrsulfuron, I+flupyrsulfuron-methyl-sodium, I+flurenol, I+fluridone, I+fluorochloridone, I+fluoroxypyr, I+flurtamone, I+fluthiacet, I+fluthiacet-methyl, I+fomesafen, I+foramsulfuron, I+fosamine, I+glufosinate, I+glufosinate-ammonium, I+glyphosate (including the potassium, isopropylammonium, sodium, trimesium, ammonium and di-ammonium salts thereof), I+halosulfuron, I+halosulfuron-methyl, I+haloxyfop, I+haloxyfop-P, I+HC-252, I+hexazinone, I+imazamethabenz, I+imazamethabenz-methyl, I+imazamox, I+imazapic, I+imazapyr, I+imazaquin, I+imazethapyr, I+imazosulfuron, I+indanofan, I+iodomethane, I+iodosulfuron, I+iodosulfuron-methyl-sodium, I+ioxynil, I+isoproturon, I+isouron, I+isoxaben, I+isoxachlortole, I+isoxaflutole, I+isoxapyrifop, I+karbutilate, I+lactofen, I+lenacil, I+linuron, I+MAA, I+MAMA, I+MCPA, I+MCPA-thioethyl, I+MCPB, I+mecoprop, I+mecoprop-P, I+mefenacet, I+mefluidide, I+mesosulfuron, I+mesosulfuron-methyl, I+mesotrione, I+metam, I+metamifop, I+metamitron, I+metazachlor, I+methabenzthiazuron, I+methazole, I+methylarsonic acid, I+methyldymron, I+methyl isothiocyanate, I+metolachlor, I+S-metolachlor, I+metosulam, I+metoxuron, I+metribuzin, I+metsulfuron, I+metsulfuron-methyl, I+molinate, I+monolinuron, I+MSMA, I+naproanilide, I+napropamide, I+naptalam, I+neburon, I+nicosulfuron, I+n-methyl glyphosate, I+nonanoic acid, I+norflurazon, I+oleic acid (fatty acids), I+orbencarb, I+orthosulfamuron, I+oryzalin, I+oxadiargyl, I+oxadiazon, I+oxasulfuron, I+oxaziclomefone, I+oxyfluorfen, I+paraquat, I+paraquat dichloride, I+pebulate, I+pendimethalin, I+penoxsulam, I+pentachlorophenol, I+pentanochlor, I+pentoxazone, I+pethoxamid, I+petrolium oils, I+phenmedipham, I+picloram, I+picolinafen, I+pinoxaden, I+piperophos, I+pretilachlor, I+primisulfuron, I+primisulfuron-methyl, I+prodiamine, I+profoxydim, I+prohexadione-calcium, I+prometon, I+prometryn, I+propachlor, I+propanil, I+propaquizafop, I+propazine, I+propham, I+propisochlor, I+propoxycarbazone, I+propoxycarbazone-sodium, I+propyzamide, I+prosulfocarb, I+prosulfuron, I+pyraclonil, I+pyraflufen, I+pyraflufen-ethyl, I+pyrasulfotole, I+pyrazolynate, I+pyrazosulfuron, I+pyrazosulfuron-ethyl, I+pyrazoxyfen, I+pyribenzoxim, I+pyributicarb, I+pyridafol, I+pyridate, I+pyriftalid, I+pyriminobac, I+pyriminobac-methyl, I+pyrimisulfan, I+pyrithiobac, I+pyrithiobac-sodium, I+pyroxasulfone, I+pyroxsulam, I+quinclorac, I+quinmerac, I+quinoclamine, I+quizalofop, I+quizalofop-P, I+rimsulfuron, I+sethoxydim, I+siduron, I+simazine, I+simetryn, I+SMA, I+sodium chlorate, I+sulcotrione, I+sulfentrazone, I+sulfometuron, I+sulfometuron-methyl, I+sulfosate, I+sulfosulfuron, I+sulfuric acid, I+tar oils, I+2,3,6-TBA, I+TCA, I+TCA-sodium, I+tebuthiuron, I+tefuryltrione, I+tembotrione, I+tepraloxydim, I+terbacil, I+terbumeton, I+terbuthylazine, I+terbutryn, I+thenylchlor, I+thiazopyr, I+thifensulfuron, I+thiencarbazone, I+thifensulfuron-methyl, I+thiobencarb, I+topramezone, I+tralkoxydim, I+tri-allate, I+triasulfuron, I+triaziflam, I+tribenuron, I+tribenuronmethyl, I+triclopyr, I+trietazine, I+trifloxysulfuron, I+trifloxysulfuron-sodium, I+trifluralin, I+triflusulfuron, I+triflusulfuron-methyl, I+trihydroxytriazine, I+trinexapacethyl, I+tritosulfuron, I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), and I+4-hydroxy-3-[[2-(3-methoxypropyl)-6-(difluoromethyl)-3-pyridinyl]carbonyl]-bicyclo[3.2.1]oct-3-en-2-one. In a preferred embodiment the additional herbicide is selected from the group consisting of ametryn, terbuthylazine, atrazine, alachlor, acetochlor, fomesafen, mesotrione, dicamba, nicosulfuron, rimsulfuron, hexazinone, metolachlor, S-metolachlor, glufosinate and glyphosate. In another embodiment the composition may comprise three active ingredients, for example a compound of Formula I+glyphosate+a third active ingredient (in particular atrazine, terbuthylazine and/or S-metolachlor).

The mixing partners of the compound of formula I may also be in the form of esters or salts, as mentioned e.g. in The Pesticide Manual, Fourteenth Edition, British Crop Protection Council, 2006.

The compound of formula I (alone or in mixture with other herbicides) can also be used in mixtures with other agrochemicals such as fungicides or insecticides, examples of which are given in The Pesticide Manual.

The mixing ratio of the compound of formula I to the mixing partner is preferably from 1:100 to 1000:1.

The compositions of the present invention may further comprise one or more herbicide safeners, for example AD 67 (MON 4660), benoxacor, cloquintocet-mexyl, cyprosulfamide (CAS RN 221667-31-8), dichlormid, fenchlorazole-ethyl, fenclorim, fluxofenim, furilazole and the corresponding R isomer, isoxadifen-ethyl, mefenpyr-diethyl, oxabetrinil, N-isopropyl-4-(2-methoxy-benzoylsulfamoyl)-benzamide (CAS RN 221668-34-4) and 2-methoxy-N-[[4-[[(methylamino)carbonyl]amino]phenyl]-sulfonyl]-benzamide (CAS RN 129531-12-0).

The safeners of the compound of formula I may also be in the form of esters or salts, as mentioned e.g. in The Pesticide Manual, 14$^{th}$ Edition (BCPC), 2006. The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048, and the reference to fenchlorazole-ethyl also applies to fenchlorazole.

Preferably the mixing ratio of compound of formula I to safener is from 100:1 to 1:10, especially from 30:1 to 1:1.

For the avoidance of doubt the term "application" as used herein includes, for example, pre-emergence and/or post-emergence application (of the crop and/or weeds). 'Locus' means the area in which the plants are growing or will grow. In a preferred embodiment the composition of the present invention is applied post-emergence.

The application is generally made by spraying the composition, typically by tractor mounted sprayer or other commercial sprayers for large areas, but other methods such as dusting (for powders), drip or drench can also be used.

Crop plants in which the composition according to the invention can be used include cereals, for example barley and wheat, cotton, oilseed rape, maize, rice, soybeans, sugar beet and sugar cane. Particularly preferred is maize and sugarcane.

Crop plants can also include trees (such as fruit trees, palm trees, coconut trees or other nuts), vines such as grapes, fruit bushes, fruit plants and vegetables.

Crops are to be understood as also including those crops which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. drought tolerance, improved storage stability, higher nutritional value and improved flavour).

Other useful plants include turf grass for example in golf-courses, lawns, parks and roadsides, or grown commercially for sod, and ornamental plants such as flowers or bushes.

The compositions can be used to control unwanted plants including grasses and broadleaf plants (collectively, 'weeds'). The weeds to be controlled may be both monocotyledonous species, for example *Agrostis, Alopecurus, Avena, Brachiaria, Bromus, Commelina, Cyperus, Digitaria, Echinochloa, Eriochloa, Lolium, Monochoria, Panicum, Rottboellia, Sagittaria, Scirpus, Setaria,* and *Sorghum,* and dicotyledonous species, for example *Abutilon, Amaranthus, Ambrosia, Bidens, Capsella, Chenopodium, Chrysanthemum, Datura, Euphorbia, Galium, Ipomoea, Kochia, Matricaria, Mercurialis, Nasturtium, Polygonum, Sida, Sinapis, Solanum, Stellaria, Veronica, Viola* and *Xanthium*. Weeds can also include plants which may be considered crop plants but which are growing outside a crop area ('escapes'), or which grow from seed left over from a previous planting of a different crop ('volunteers'). Such volunteers or escapes may be tolerant to certain other herbicides.

Agriculturally acceptable salts that the compound of formula I is able to form with, for example, amines, alkali metal and alkaline earth metal bases or quaternary ammonium bases are also included in the method of the present invention. Among the alkali metal and alkaline earth metal hydroxides as salt formers, special mention should be made of the hydroxides of lithium, sodium, potassium, magnesium and calcium, but especially the hydroxides of sodium and potassium.

Examples of amines suitable for ammonium salt formation include ammonia as well as primary, secondary and tertiary $C_1$-$C_{18}$alkylamines, $C_1$-$C_4$hydroxyalkyl-amines and $C_2$-$C_4$alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-butylamine, di-n-amylamine, diisoamyl-amine, dihexylamine, diheptylamine, dioctylamine, ethanolamine, n-propanolamine, isopropanolamine, diethanolamine, triethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloro-anilines.

The aqueous spray composition used in the method of the present invention may be provided as a "tank mix"—whereby a concentrated herbicidal composition comprising a compound of formula (I) is typically diluted and the pH adjusted as necessary in the tank. Alternatively, a concentrated herbicidal composition may be provided with a built-in pH adjuster which, when diluted, provides an aqueous spray composition of the necessary pH.

Thus, according to the present invention there is further provided a liquid substantially non-aqueous herbicidal composition comprising:—
(a) a compound of formula I

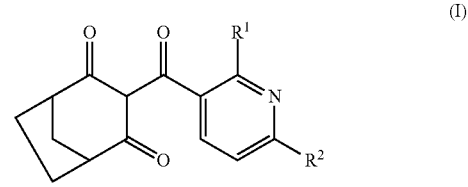

wherein $R^1$ is selected from the group consisting of $C_1$-$C_6$alkyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl, $C_1$-$C_6$-haloalkyl, $C_1$-$C_4$alkoxy-$C_1$-$C_4$alkyl and $C_1$-$C_4$alkoxy-$C_1$-$C_4$alkoxy-$C_1$-$C_4$alkyl; and
$R^2$ is $C_1$-$C_6$haloalkyl;
or an agriculturally acceptable salt therefore; and
(b) a pH adjuster;
wherein the pH adjuster is present in the liquid substantially non-aqueous herbicidal composition in an amount effective for providing an aqueous spray composition having a pH from about 5 to about 9 when the liquid non-aqueous herbicidal composition is combined with water and/or an aqueous solution.

Alternatively, the concentrated herbicide composition can be provided in a solid form—for example a granule, water soluble granule, dust, powder or a micro-capsule etc—wherein the solid form is added to the spray tank and the pH adjusted as necessary. Of course, it is possible for the solid composition to conveniently further include the pH adjuster.

The pH adjuster can be any substance that provides the desired pH range in the aqueous spray solution. Typically the pH adjuster will be a base and thus examples of suitable pH adjusters include amines, alkali metal and alkaline earth metal bases or quaternary ammonium bases as mentioned previously that are capable of forming salts with the compound of formula (I). It should also be understood that where the composition comprises a second pesticide then it is possible that the second pesticide can be the pH adjuster. Examples of suitable amines include N-tert-butylisopropylamine, tripropylamine, n,n-diisopropylethylamine (Huenig's base), 2,2,6,6-tetramethylpiperidine, diethanolamine, diethylamine, diethylenetriamine, diethylethanolamine, diethylhydroxylamine, diisopropanolamine, dimethylamine, dimethylcyclohexanamine, ethanolamine, ethyl ethanolamine, ethylenediamine, hexamethylenetetramine, isopropylamine, monoisopropanolamine, tetraethylenepentamine, triethanolamine, triethanolamine phosphate, triethylamine, triethylamine phosphate, triethylenetetramine, tri-isopropanolamine, trimethylamine, glutamine, hexamethylenetetramine and primary n-alkylamines, where the alkyl group (C8-C18) is derived from coconut, cottonseed, soya, or tallow acids. It is particularly preferred that the pH adjuster is diethanolamine or triethanolamine.

The skilled person will appreciate that the amount of pH adjuster required in the liquid non-aqueous herbicidal composition to provide the desired pH in the aqueous spray solution will depend on a number of determinable factors, including the volume of the liquid non-aqueous herbicidal composition, the concentration and exact nature of the compound of formula (I) in the composition, and the envisaged dilution of the non-aqueous composition necessary to provide the aqueous composition.

The term "liquid substantially non-aqueous herbicidal composition" is taken to mean a liquid herbicidal composition which contains no water or only very small amounts of water (e.g. <5% v/v, preferably less than 1% v/v). The skilled man will appreciate that small quantities of water such as this may be present in the composition due to it being present in small quantities in, for example, any of the ingredients present in the composition. Examples of liquid non-aqueous herbicidal compositions include emulsifiable concentrates and oil miscible flowable concentrates (oil dispersions).

The skilled person will appreciate that many solvents can be used with regard to the liquid substantially non-aqueous herbicidal compositions. Suitable solvents may typically be: aromatic hydrocarbons, preferably the fractions containing 8 to 12 carbon atoms such as mixtures of xylene or substituted naphthalenes; phthalates such as dibutyl phthalate or dactyl phthalate; aliphatic hydrocarbons such as cyclohexane or paraffins; alcohols and glycols and their ethers and esters such as ethanol, ethylene glycol, 2-methoxyethanol or 2-ethoxyethanol; ketones such as cyclohexanone, strongly polar solvents such as N-methyl-2-pyrrolidone, dimethylsulfoxide or N,N-dimethylformamide, as well as vegetable oils or epoxidised vegetable oils such as epoxidised coconut oil or soybean oil. In a preferred embodiment the solvent is propylene carbonate or acetophenone.

It is understood that the liquid non-aqueous herbicidal composition may also comprise an additional pesticide and/or herbicide safener as previously defined.

In a preferred embodiment the non-aqueous herbicidal composition is an emulsifiable concentrate which comprises a compound of formula (I) and a chloroacetanilide, preferably S-metolachlor, and wherein the pH adjuster is a secondary amine, preferably diethanolamine. In another embodiment, the non-aqueous herbicidal composition is an oil dispersion which comprises the sodium or potassium salt of a compound of formula (I).

The skilled person will recognise that the compositions of the present invention may typically include one or more additives (adjuvants) to improve the biological performance of the composition, for example by improving wetting, retention or distribution on surfaces; resistance to rain on treated surfaces; or uptake or mobility of a compound of formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of formula (I)).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octyl-cresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

Thus, in a preferred embodiment of the present invention the herbicide composition further comprises a SFA (adjuvant). Particularly preferred adjuvants with regard to the herbicidal composition of the present invention include Tristyrylphenol (16) Ethoxylate (Soprophor BSU™), Tristyrylphenol ethoxylate phosphate ester (Soprophor 3D33™), Polyoxyethylene (10) Oleyl Ether (Genapol™ O-100), Polyoxyethylene (15) Oleyl Ether (Genapol™ O-150), Polyoxyethylene (20) Oleyl Ether (Genapol™ O-200), Crop Oil (Petroleum) Concentrate (AGRI-DEX™), Organo-Silicone Surfactant Polyalkyleneoxide modified heptamethylsiloxane (SILWET L-77™), PEG(20) sorbitan monolaurate (Tween 20™), Octyl/decyl alkylpolyglycoside (Agnique PG 8107™). Especially preferred are Genapol™ O-100 and Soprophor BSU™.

The present invention still further provides the use of a pH adjuster to reduce the phytotoxicity of a compound of formula I

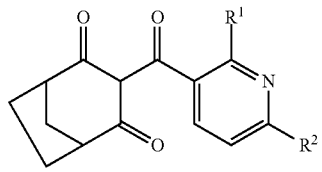

(I)

wherein R¹ is selected from the group consisting of C$_1$-C$_6$alkyl, C$_2$-C$_6$alkenyl, C$_2$-C$_6$haloalkenyl, C$_2$-C$_6$alkynyl, C$_2$-C$_6$haloalkynyl, C$_3$-C$_6$cycloalkyl, C$_1$-C$_6$-haloalkyl, C$_1$-C$_4$alkoxy-C$_1$-C$_4$alkyl and C$_1$-C$_4$alkoxy-C$_1$-C$_4$alkoxy-C$_1$-C$_4$alkyl; and R² is C$_1$-C$_6$haloalkyl;

in crop plants.

EXAMPLES

Provided below are examples of compositions of the present invention Examples 1-7 provide examples of non-aqueous herbicidal compositions (emulsifiable concentrates). The various components listed in the tables are mixed and stirred until full dissolution is achieved. Compound A=a compound of Formula (I) wherein R¹=methoxy-ethyoxy-methyl and R²=CF$_3$.

Example 1

| Constituent Name | g/L |
| --- | --- |
| Compound A | 150 |
| Triethanolamine | 100 |
| Soprophor BSU ™ | 20 |
| Castor oil (36) ethoxylate (Emulsogen EL360 ™) | 60 |
| Calcium dodecylbenzene sulphonate (Nansa EVM63B ™) | 40 |
| Genapol O-100 ™ | 200 |
| Antifoam | 0.3 |
| Propylene carbonate | 300 |
| Aromatic hydrocarbons (Solvesso 200 ND ™). | To 1 liter |

Example 2

| Constituent Name | g/L |
| --- | --- |
| Compound A | 80 |
| S-Moc | 400 |
| Diethanolamine | 32 |
| Soprophor BSU ™ | 150 |
| Nansa EVM63B ™ | 40 |
| Antifoam | 0.3 |
| Propylene carbonate | 200 |
| Solvesso 200 ND ™ | To 1 liter |

Example 3

| Constituent Name | g/L |
| --- | --- |
| Compound A | 150 |
| Soprophor BSU ™ | 320 |
| Emulsogen EL360 ™ | 60 |
| Nansa EVM63B ™ | 40 |
| Antifoam | 0.3 |
| Triethanol amine | 100 |
| Acetophenone | 300 |
| Solvesso 200 ND ™ | To 1 liter |

Example 4

| Constituent Name | g/L |
| --- | --- |
| Compound A | 80 |
| S-metolachlor | 400 |
| Soprophor BSU ™ | 90 |
| Nansa EVM63B ™ | 40 |
| Genapol O-100 ™ | 130 |
| Diethanolamine | 32 |
| Antifoam | 0.3 |
| Propylene carbonate | 200 |
| Solvesso 200 ND ™ | To 1 liter |

Example 5

| Constituent Name | g/L |
| --- | --- |
| Compound A | 100 |
| S-metolachlor | 500 |
| Soprophor BSU ™ | 90 |
| Nansa EVM63B ™ | 40 |
| Diethanolamine | 40 |
| Antifoam | 0.3 |
| Propylene carbonate | 200 |
| Solvesso 200 ND ™ | To 1 liter |

Example 6

| Constituent Name | g/L | Role |
| --- | --- | --- |
| Compound A | 300 | TGAI |
| Triethanolamine | 120 | Alkali |
| Soprophor BSU ™ | 20 | Emulsifier |
| Emulsogen EL360 ™ | 60 | Emulsifier |
| Nansa EVM63B ™ | 40 | Emulsifier |
| Antifoam | 0.3 | Antifoam |
| Propylene carbonate | 200 | Solvent |
| Solvesso 200 ND ™ | To 1 liter | Make-up solvent |

Examples 8 and 9 provide examples of soluble concentrate compositions. These compositions are produced by first reacting together the potassium hydroxide and compound A in water to form a 20% w/w concentrate at pH=8, which is then finalised by addition of the other ingredients.

Example 8

| Constituent Name | g/L |
| --- | --- |
| Compound A | 150 |
| Potassium Hydroxide (45%) Solution | 46.8 g/L |
| Genapol O-100 ™ | 200 g/L |
| Antifoam | 0.5 |
| Water | To 1 Liter |

Example 9

| Constituent Name | g/L |
| --- | --- |
| Compound A | 150 |
| Potassium Hydroxide (45%) Solution | 46.8 g/L |
| Soprophor BSU ™ | 300 g/L |
| Antifoam | 0.5 |
| Water | To 1 Liter |

Examples 10 and 11 provide examples of oil dispersion compositions. To prepare these formulations the oil-insoluble sodium salt of compound A is first isolated by precipitating it following reaction of excess sodium hydroxide and compound A in an aqueous environment. Once the sodium salt of compound A is isolated, it is then milled into the oil using the dispersants followed by addition of the anti-settling system (Bentone 38™ activated by propylene carbonate).

Example 10

| Constituent Name | g/L |
| --- | --- |
| Compound A as 1:1 Na salt* | 159 |
| Alkylated vinylpyrrolidone copolymer (Agrimer AL-22 ™) | 25 |
| Oleyl/cetyl alcohol (5) polyglycol ether (Emulsogen M ™) | 75 |
| Propylene glycol n-butyl ether (Arcosolv PNB ™) | 20 |
| Organophilic Clay; Tetraalkyl ammonium hectorite (Bentone 38 ™). | 10 |
| Propylene carbonate | 1 |
| Refined heavy paraffinic petroleum oil (Sunspray 11N ™). | To 1 liter |

*this equates to 150 g/L of the compound A acid equivalent

Example 11

| Constituent Name | g/L |
| --- | --- |
| Compound A as 1:1 Na salt* | 106 |
| S-metolachlor | 500 |
| Agrimer AL-22 ™ | 25 |
| Emulsogen M ™ | 75 |
| Arcosolv PNB ™ | 20 |
| Bentone 38 ™ | 10 |
| Propylene carbonate | 1 |
| Sunspray 11N ™ | To 1 liter |

*this equates to 100 g/L of the compound A acid equivalent

Biological Comparisons

Experiment 1.

The following compositions were prepared in order to conduct biological comparisons.

TABLE A

| | Test Formulation 1 (% w/v) | Test Formulation 2 (% w/v) |
| --- | --- | --- |
| Compound A | 10 | 10 |
| Emulsogen EL ™ | 6 | 6 |
| Non-ionic surfactant: octyl phenol (8) ethoxylate (Extravon ™) | 50 | 50 |
| Semul EA 80 ™ | 4 | 4 |
| Soprophor BSU ™ | 2 | 2 |
| N-methyl-Pyrrolidone | 35.4 | — |
| Acetophenone | — | 34.2 |

Compound A = a compound of Formula (I) wherein $R^1$ = methoxy-ethyoxy-methyl and $R^2$ = $CF_3$.

A field trial was conducted to look at the effect of pH of the spray composition on the selectivity of the EC formulations described in Table A. Applications were made early POST emergence using the corn variety "Marista" and three grass weeds *Echinochloa crus-galli* (ECHCG), *Setaria faberi* (SETFA) and *Brachiaria plantaginea* (BRAPL)). Results are provided in Table B as % phytotoxicity observed wherein 0=no visible phytotoxicity to 100=complete phytotoxicity.

TABLE B

| | [Compound A] g ai/ha | | Corn "Marista" | ECHCG | SETFA | BRAPL |
| --- | --- | --- | --- | --- | --- | --- |
| Formulation 1 | 400 | pH 3 | 30 | — | — | — |
| | | pH 5 | 20 | — | — | — |
| | | pH 8 | 15 | — | — | — |
| | 200 | pH 3 | 20 | 90 | 85 | 85 |
| | | pH 5 | 10 | 100 | 98 | 90 |
| | | pH 8 | 0 | 100 | 100 | 95 |
| Formulation 2 | 400 | pH 3 | 40 | — | — | — |
| | | pH 5 | 20 | — | — | — |
| | | pH 8 | 20 | — | — | — |
| | 200 | pH 3 | 25 | 90 | 95 | — |
| | | pH 5 | 10 | 100 | 100 | 100 |
| | | pH 8 | 10 | 100 | 100 | 95 |

These results show that both formulations tested showed decreasing phytotoxicity in the crop (corn) with increasing pH and, in the majority of cases, increasing control in the weeds with increasing pH—thus providing an unexpected overall improvement in selectivity of compound A.

Experiment 2.

A greenhouse trial was conducted to look at the effect of pH on the selectivity of an emulsifiable concentrate composition comprising compound B (compound of formula wherein $R^1$=methoxy-propyl and $R^2$=$CHF_2$). Applications were made early POST using four corn varieties and eight weeds (Broad leaf weeds: *Amaranthus retroflexus* (AMARE), *Ipomoea hederacea* (IPOHE), *Polygonum convolvulus* (POLCO) Grasses: *Digitaria sanuinalis* (DIGSA), *Echinochloa crus-galli* (ECHCG), *Eriochloa villosa* (ERBVI), *Panicum dichotomiflorum* (PANDI), *Setaria viridus* (SETVI)). The spray volume applied was 200 l/ha. Phytotoxicity evaluations were made 8 days after application (DAA) and/or 28 DAA. Results are provided as % phytotoxicity observed wherein 0=no visible phytotoxicity to 100=complete phytotoxicity.

TABLE C

Biological results obtained with various corn varieties

| Compound B g ai/ha | | Corn "Marista" | | Corn "Cecilia" | | Corn "Lorenzo" | | Corn "Blizzard" | |
|---|---|---|---|---|---|---|---|---|---|
| | | 8 DAA | 28 DAA | 8 DAA | 28 DAA | 8 DAA | 28 DAA | 8 DAA | 28 DAA |
| 200 | pH 3 | 30 | 15 | 20 | 20 | 30 | 30 | 25 | 20 |
| | pH 8 | 5 | 5 | 20 | 10 | 25 | 25 | 20 | 10 |
| 100 | pH 3 | 5 | 5 | 5 | 10 | 20 | 25 | — | 10 |
| | pH 8 | 5 | 5 | 5 | 10 | 20 | 20 | — | 10 |

TABLE D

Biological results obtained with various weed species.

| Compound B G ai/ha | | AMARE 8 DAA | IPOHE 8 DAA | POLCO 8 DAA | DIGSA 8 DAA | ECHCG 8 DAA | ERBVI 8 DAA | PANDI 8 DAA | SETVI 8 DAA |
|---|---|---|---|---|---|---|---|---|---|
| 200 | pH 3 | 100 | 95 | 95 | 100 | 98 | 90 | 100 | 100 |
| | pH 8 | 98 | 90 | 90 | 95 | 95 | 98 | 100 | 98 |
| 100 | pH 3 | 98 | 80 | 80 | 85 | 80 | 80 | 98 | 90 |
| | pH 8 | 95 | 85 | 70 | 85 | 95 | 98 | 98 | 90 |

The results presented in Table C shows that the phytotoxicity observed in corn is significantly decreased when the herbicide of formula B is applied at pH 8 rather than pH 3.

The invention claimed is:

1. A method of improving the selective weed control of a compound of formula I, at a locus comprising crop plants and weeds, wherein the method comprises application to the locus of a weed a controlling amount of an aqueous spray composition comprising (i) 200-400 g/ha of the compound of formula I (I)

wherein $R^1$ is methoxy-ethoxy-methyl-; and $R^2$ is $CF_3$; or an agriculturally acceptable salt thereof, (ii) an optional additional pesticide, and (iii) a pH adjuster, wherein the pH adjuster is triethanolamine or diethanolamine; and wherein the pH of the spray composition is from about 5 to about 8; and wherein the pH adjuster within the aqueous spray composition decreases the phytotoxicity of the compound of formula I to the crop plants.

2. The method according to claim 1, wherein the aqueous spray composition comprises the additional pesticide.

3. The method according to claim 2, wherein the additional pesticide is a herbicide selected from the group consisting of ametryn, terbuthylazine, atrazine, alachlor, acetochlor, fomesafen, mesotrione, dicamba, nicosulfuron, rimsulfuron, hexazinone, metolachlor, S-metolachlor, glufosinate and glyphosate.

4. The method according to claim 1, wherein the crop plant is selected from the group consisting of cereals, cotton, oilseed rape, maize, rice, soybeans, sugar beet and sugar cane.

5. The method according to claim 4, wherein the crop plant is COM.

6. The method according to claim 1, wherein the application is made post-emergence of the crop.

7. A liquid herbicidal composition having less than 5% v/v water comprising:

(a) a compound of formula I

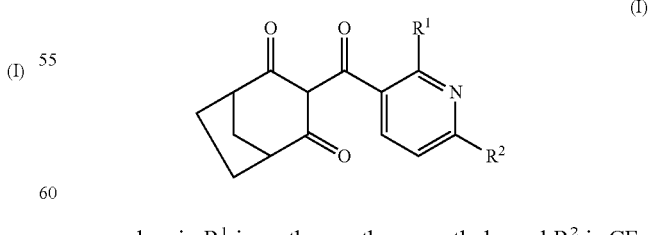

(I)

wherein $R^1$ is methoxy-ethoxy-methyl-; and $R^2$ is $CF_3$ or an agriculturally acceptable salt thereof, said compound of formula I being present in an amount ranging from about 80 to about 300 g/L of said liquid herbicidal composition; and (b) an optional additional pesticide; and (c) a pH adjuster, wherein the pH adjuster is triethanolamine or diethanolamine; wherein the pH adjuster is present in the liquid herbicidal composition in an amount effective for providing a spray composition having pH of from about 5 to about 8 when the liquid herbicidal composition is combined with water and/or an aqueous solution.

8. The liquid herbicidal composition according to claim 7, which is an emulsifiable concentrate.

9. The liquid herbicidal composition according to claim 7, which comprises the additional pesticide.

10. The liquid herbicidal composition according to claim 9, wherein the additional pesticide is a herbicide selected from the group consisting of ametryn, terbuthylazine, atrazine, alachlor, acetochlor, fomesafen, mesotrione, dicamba, nicosulfuron, rimsulfuron, hexazinone, metolachlor, S-metolachlor, glufosinate and glyphosate.

11. The liquid herbicidal composition according to claim 9 further comprising a herbicide safener.

* * * * *

UNITED STATES PATENT AND TRADEMARK OFFICE
CERTIFICATE OF CORRECTION

PATENT NO.         : 9,456,604 B2                                    Page 1 of 1
APPLICATION NO.    : 12/997217
DATED              : October 4, 2016
INVENTOR(S)        : Jeffrey D. Fower et al.

It is certified that error appears in the above-identified patent and that said Letters Patent is hereby corrected as shown below:

Column 14, Claim 5, Line 45: the word "COM" should be changed to -corn-.

Signed and Sealed this
Twenty-eighth Day of February, 2017

Michelle K. Lee
*Director of the United States Patent and Trademark Office*